(12) United States Patent
Anderson et al.

(10) Patent No.: US 8,064,978 B2
(45) Date of Patent: Nov. 22, 2011

(54) MODULAR CATHETER

(75) Inventors: Neil L. Anderson, Roseville (AU); Evan K. Chong, Roseville (AU); Matthew J. Partlett, Allawah (AU)

(73) Assignee: Cathrx Ltd, Homebush Bay, NSW (AT)

( * ) Notice: Subject to any disclaimer, the term of this patent is extended or adjusted under 35 U.S.C. 154(b) by 951 days.

(21) Appl. No.: 10/580,636

(22) PCT Filed: Nov. 24, 2004

(86) PCT No.: PCT/AU2004/001638
§ 371 (c)(1),
(2), (4) Date: Sep. 4, 2007

(87) PCT Pub. No.: WO2005/051216
PCT Pub. Date: Jun. 9, 2005

(65) Prior Publication Data
US 2008/0045921 A1    Feb. 21, 2008

Related U.S. Application Data

(60) Provisional application No. 60/525,450, filed on Nov. 25, 2003.

(51) Int. Cl.
*A61B 5/042* (2006.01)
*A61B 18/14* (2006.01)
(52) U.S. Cl. ............ 600/373; 600/374; 600/381; 606/41
(58) Field of Classification Search .......... 600/374–393; 606/32–52
See application file for complete search history.

(56) References Cited

U.S. PATENT DOCUMENTS

| | | |
|---|---|---|
| 3,416,531 A | 12/1968 | Lowell |
| 3,552,384 A | 1/1971 | Pierie et al. |
| 4,101,984 A | 7/1978 | MacGregor |
| 4,799,474 A | 1/1989 | Ueda |

(Continued)

FOREIGN PATENT DOCUMENTS

EP    0 479 435 A3    8/1990

(Continued)

OTHER PUBLICATIONS

Supplementary Partial European Search Report mailed on Feb. 12, 2007, for EP Application No. 01977995.8, filed on Oct. 19, 2001, five pages.

(Continued)

*Primary Examiner* — Linda Dvorak
*Assistant Examiner* — Erin Cardinal
(74) *Attorney, Agent, or Firm* — TraskBritt

(57) ABSTRACT

A modular catheter includes an elongate tubular member having a proximal end and a closed, distal end. A lumen extends from the proximal end to the distal end and a plurality of electrodes are arranged at, or adjacent, the distal end, conductors for the electrodes being contained within a wall of the tubular member. An elongate shape-imparting mechanism is removably received within the lumen of the tubular member such that a distal end of the shape-imparting mechanism is substantially in register with the distal end of the tubular member. A control device has a proximal end and a distal end, the proximal end of the tubular member and a proximal end of the shape-imparting mechanism being releasably connectable to the distal end of the control device.

11 Claims, 4 Drawing Sheets

U.S. PATENT DOCUMENTS

| | | | |
|---|---|---|---|
| 5,269,810 A | 12/1993 | Hull et al. | |
| 5,396,902 A * | 3/1995 | Brennen et al. | 600/585 |
| 5,487,757 A | 1/1996 | Truckai et al. | |
| 5,514,131 A * | 5/1996 | Edwards et al. | 606/45 |
| 5,522,874 A | 6/1996 | Gates | |
| 5,834,051 A | 11/1998 | Woloszko et al. | |
| 5,860,953 A | 1/1999 | Snoke et al. | |
| 5,861,024 A | 1/1999 | Rashidi | |
| 5,924,977 A * | 7/1999 | Yabe et al. | 600/121 |
| 5,931,862 A | 8/1999 | Carson | |
| 6,007,531 A * | 12/1999 | Snoke et al. | 606/15 |
| 6,071,278 A | 6/2000 | Panescu et al. | |
| 6,221,070 B1 | 4/2001 | Tu et al. | |
| 7,178,234 B2 | 2/2007 | Kawasaki et al. | |

FOREIGN PATENT DOCUMENTS

| | | |
|---|---|---|
| EP | 0 479 435 A2 | 9/1991 |
| JP | 07-505317 | 6/1995 |
| JP | 2002-516729 | 6/2002 |
| SE | 156 901 | 11/1956 |
| WO | WO-90/08466 A1 | 8/1990 |
| WO | WO-96/36860 A2 | 11/1996 |
| WO | WO-96/36860 A3 | 11/1996 |
| WO | 02/32497 A1 | 4/2002 |

OTHER PUBLICATIONS

International Search Report mailed Dec. 22, 2004, for PCT Application No. PCT/AU2004/001638, filed Nov. 24, 2004, four pages.

Supplementary European Search Report mailed on Oct. 21, 2010, for EP Application No. 04797086, two pages.

Japanese Search Report for JP Application No. P2006-540088, dated Jan. 26, 2010 (English translation only).

Written Opinion mailed Dec. 22, 2004, for PCT Application No. PCT/AU2004/001638, filed Nov. 24, 2004, three pages.

International Preliminary Report on Patentability dated May 29, 2006, for PCT Application No. PCT/AU2004/001638, filed Nov. 24, 2004, 4 pages.

* cited by examiner

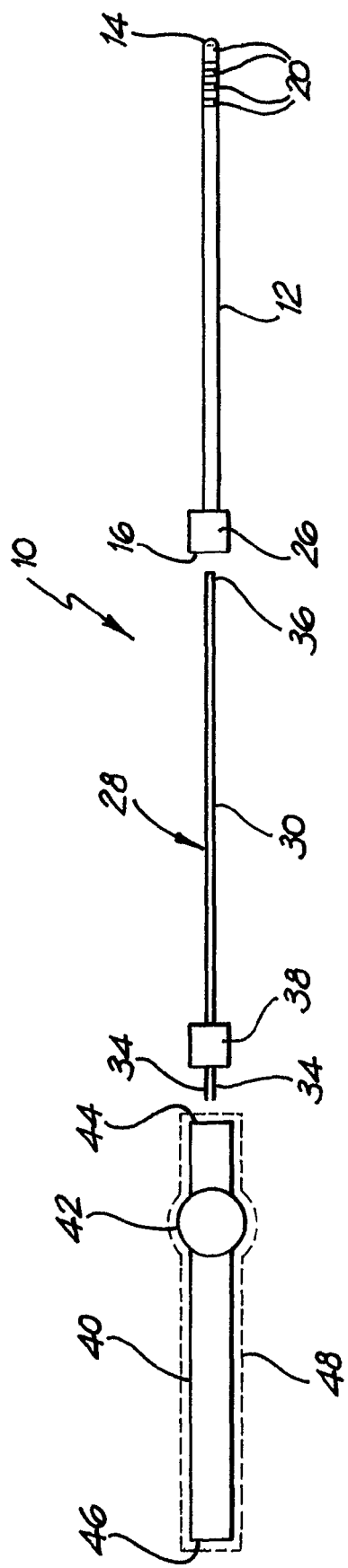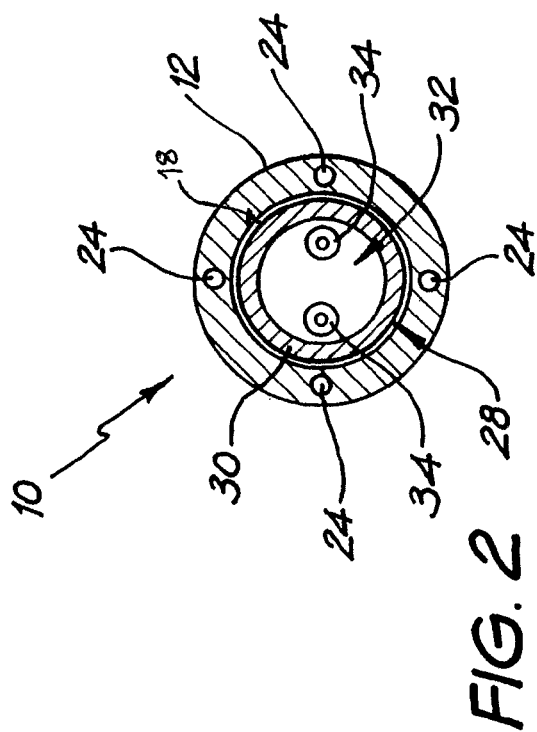

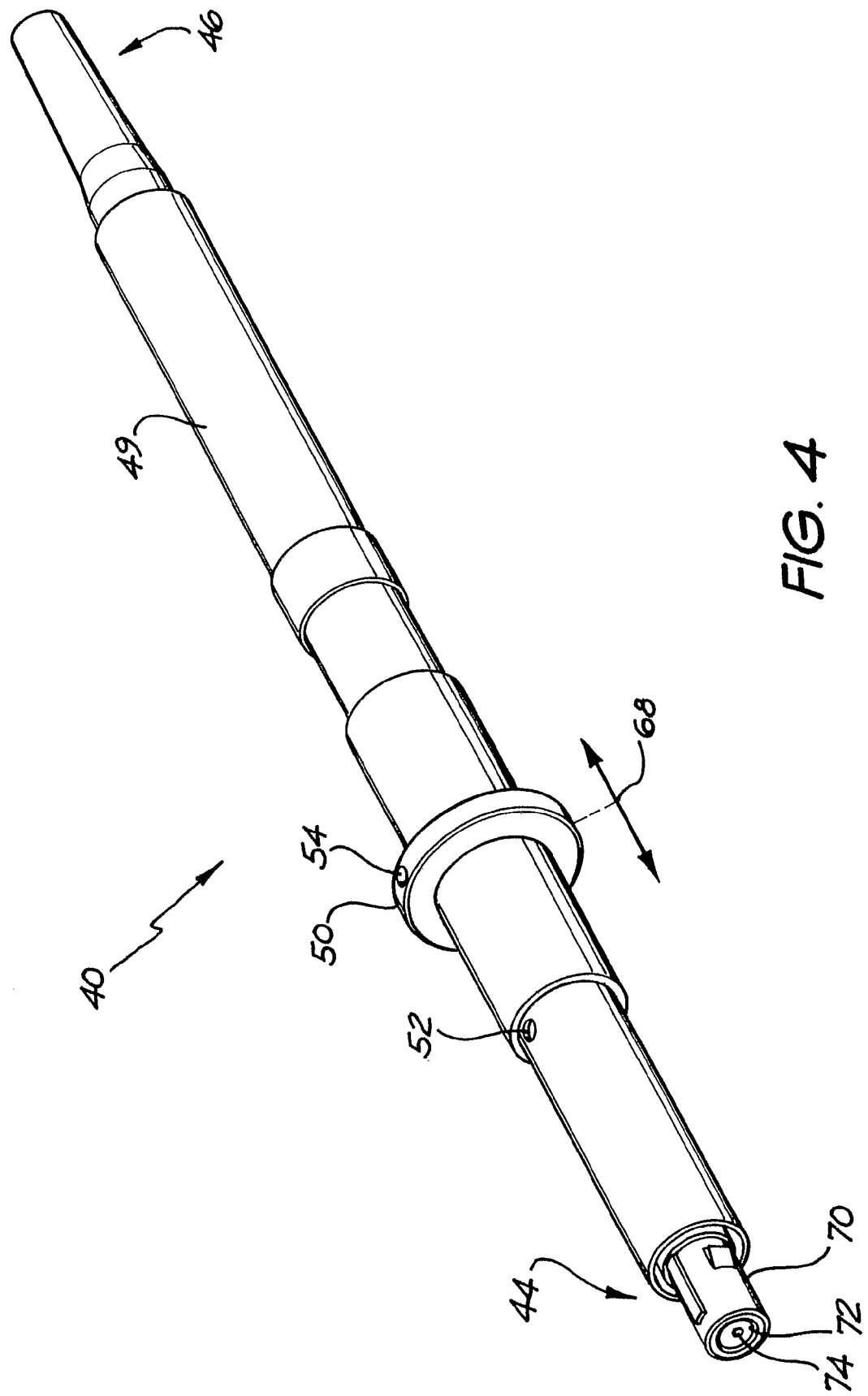

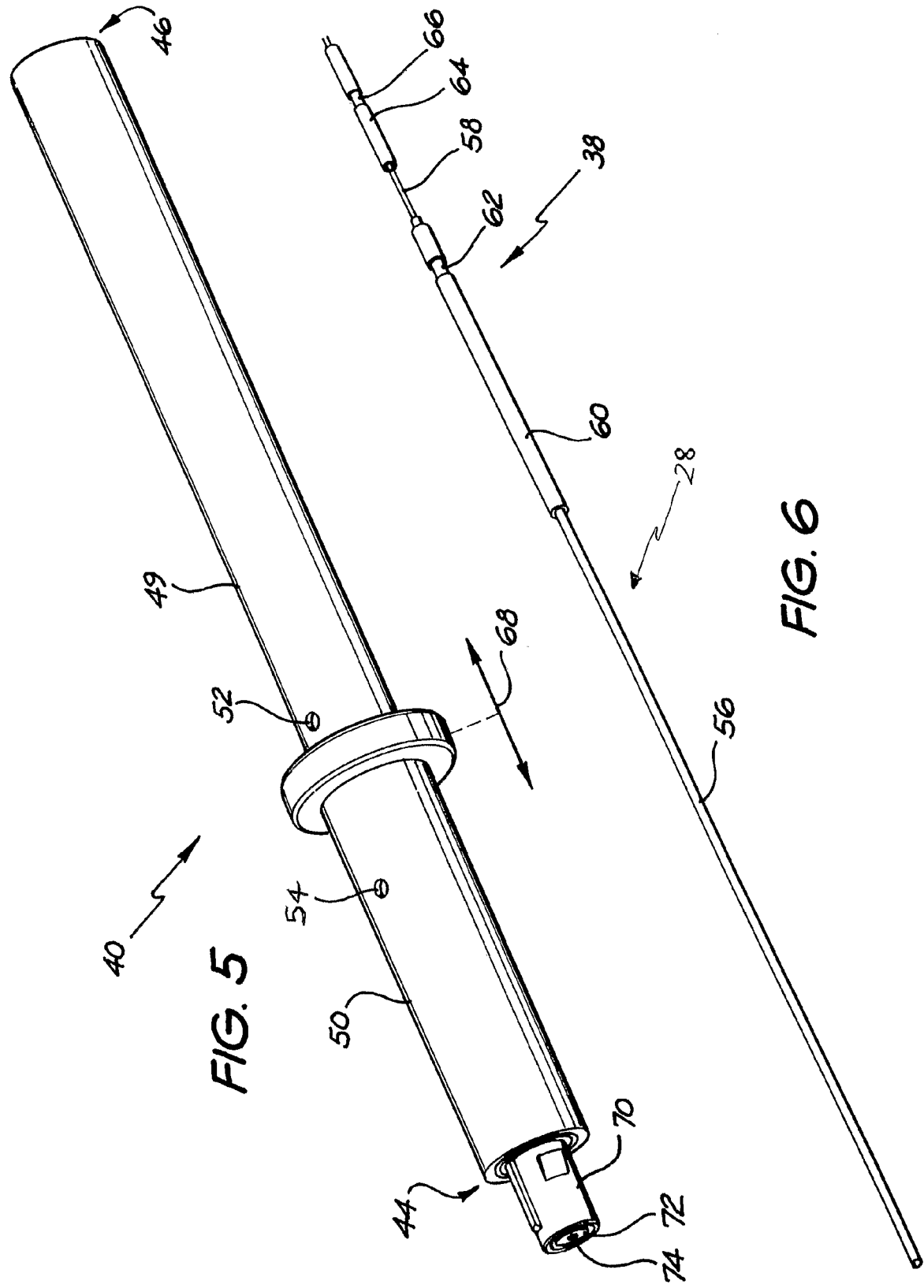

MODULAR CATHETER

CROSS-REFERENCE TO RELATED APPLICATIONS

The present application is a National Phase filing under 35 U.S.C. §371 of International Application No. PCT/AU2004/001638 filed Nov. 24, 2004, which claims priority to U.S. Provisional Patent Application No. 60/525,450 filed on Nov. 25, 2003, the contents of which are incorporated herein by reference in their entirety.

FIELD OF THE INVENTION

This invention relates to a catheter system. More particularly, the invention relates to a modular catheter.

BACKGROUND TO THE INVENTION

Catheter systems are becoming an increasingly common way of diagnosing and treating abnormal heart conditions, in particular, heart arrhythmias. Such arrhythmias can be treated with drugs or by use of electronic devices such as pacemakers. However, neither of these treatments cures the problem but only alleviate it.

In contrast, the use of ablative techniques has been shown to cure arrhythmias. Thus, catheters having mapping electrodes and/or ablative electrodes are inserted through the vascular system of a patient's body so that the distal end of the catheter can be placed accurately in the relevant chamber of the heart. For the treatment of atrial fibrillation, the distal end is placed at the ostium of one or more of the pulmonary veins, in turn, to effect ablation.

Thus, it will be appreciated that the catheter needs to be in a sterilized condition for use and various catheter systems with steering mechanisms included are known.

Because of the fact that the catheter system comes into contact with bodily fluids of a patient and with the increasing prevalence of blood-borne diseases, medical regulations require that these catheter systems are one-time-use systems only. In other words, once the catheter has been used, it must be disposed of in its entirety.

Certain institutions do re-sterilize the catheters for re-use. However, there is a problem associated with this, in that with re-sterilizing the catheter, it may become degraded and not function correctly.

In addition, the increasing complexity of catheter systems for monitoring or mapping and/or ablation has resulted in these catheter systems becoming more expensive. Thus, it is costly to dispose of such a system after one use only.

BRIEF SUMMARY

According to a first aspect of the invention, there is provided a modular catheter that includes:
  an elongate tubular member having a proximal end and a closed, distal end with a lumen extending from the proximal end to the distal end and a plurality of electrodes arranged at, or adjacent, the distal end, conductors for the electrodes being contained within a wall of the tubular member;
  an elongate shape-imparting mechanism removably received within the lumen of the tubular member, such that a distal end of the shape-imparting mechanism is substantially in register with the distal end of the tubular member; and
  a control device having a proximal end and a distal end, the proximal end of the tubular member and a proximal end of the shape-imparting mechanism being releasably connectable to the distal end of the control device.

In a preferred form of the invention, the shape-imparting mechanism and the tubular member may be releasably connectable to the control device independently of each other.

The tubular member carrying the electrodes may be a disposable element to be used once only and, thereafter, to be disposed of. The tubular member may be manufactured in accordance with the Applicant's manufacturing technique as disclosed in its PCT Publication No. WO 02/32497 entitled "An Electrical Lead," the contents of which are incorporated herein by reference. The advantage of this manufacturing technique is that an unimpeded lumen is provided with conductors for the electrodes being contained within a wall of the tubular member.

Thus, the shape-imparting mechanism, which in one form of the invention may be a manipulating mechanism, may have an outer diameter approximating that of a diameter of the lumen of the tubular member to be a snug fit within the lumen of the tubular member.

The shape-imparting mechanism may comprise a steering mechanism to effect steering of the distal end, or tip, of the tubular member for manipulating the tubular member through the vascular system of the person's body and accurately to place the tip of the tubular member in position where mapping and/or ablation is to occur.

The proximal end of the tubular member may carry a connector thereon for connection to a corresponding connector of the control device. The connector may be any suitable electro-mechanical device for effecting releasable electrical connection between the conductors in the tubular member and electrical leads in the control device and mechanical engagement between the proximal end of the tubular member and the distal end of the control device while still allowing sterilization of the handle.

Similarly, a proximal end of the shape-imparting mechanism may carry a coupling mechanism for effecting releasable mechanical coupling to the control device and to a manipulating element of the control device.

The manipulating element may be an actuator that is linearly displaceable relative to a body of the control device. The coupling mechanism of the steering mechanism may have a first securing formation releasably connectable to the body of the control device and a second securing formation releasably connectable to the actuator so that displacement of the securing formations relative to each other causes lateral displacement of the distal end of the steering mechanism and, hence, the distal end of the tubular member.

It will be appreciated that a proximal end of the control device, which may be in the form of a handle, may include electrical connectors for connection to an ECG machine and/or to a source of ablation energy such as a RF energy source.

If desired, the modular catheter may include a disposable, covering member, preferably of a plastic material, for the control device. The covering member may cover controls of the control device to inhibit the access of bodily fluids into such controls and further to enhance the hygienic nature of the catheter.

In another embodiment of the invention, where steering of the distal tip of the catheter is not required, the shape-imparting mechanism may be a stylet that is received in the lumen of the tubular member. The stylet may impart a fixed curve to the tubular member in applications where fixed curved catheters are required.

According to a second aspect of the invention, there is provided a modular catheter that includes:
an elongate tubular member having a proximal end and a closed, distal end with a lumen extending from the proximal end to the distal end and a plurality of electrodes arranged at, or adjacent, the distal end, conductors for the electrodes being contained within a wall of the tubular member;
an elongate shape-imparting mechanism removably received within the lumen of the tubular member, such that a distal end of the shape-imparting mechanism is substantially in register with the distal end of the tubular member; and
an elongate control device having a proximal end and a distal end, the proximal end of the tubular member and a proximal end of the shape-imparting mechanism being releasably connectable to the distal end of the control device, the control device carrying an actuator thereon, which is displaceable along a longitudinal axis of the control device for controlling displacement of the distal end of the shape-imparting mechanism to effect displacement of the distal end of the tubular member.

According to a third aspect of the invention, there is provided a modular catheter that includes:
an elongate tubular member having a proximal end and a closed, distal end with a lumen extending from the proximal end to the distal end and a plurality of electrodes arranged at, or adjacent, the distal end, conductors for the electrodes being contained within a wall of the tubular member;
an elongate shape-imparting mechanism removably received within the lumen of the tubular member such that a distal end of the shape-imparting mechanism is substantially in register with the distal end of the tubular member; and
a control device having a proximal end and a distal end, the proximal end of the tubular member and a proximal end of the shape-imparting mechanism being releasably connectable to the distal end of the control device, the control device including a body and an actuator displaceably arranged on the body, a proximal end of the shape-imparting mechanism carrying a first securing formation releasably connectable to the actuator and a second securing formation releasably connectable to the body.

BRIEF DESCRIPTION OF THE DRAWINGS

Embodiments of the invention are now described by way of example with reference to the accompanying drawings in which:
FIG. 1 shows a schematic, exploded view of a modular catheter, in accordance with an embodiment of the invention;
FIG. 2 shows a schematic, sectional end view of part of the modular catheter of FIG. 1;
FIG. 4 shows a three-dimensional view of a control device of another embodiment of a modular catheter;
FIG. 5 shows a three-dimensional view of a control device of yet a further embodiment of a modular catheter;
and
FIG. 6 shows a three-dimensional view of a proximal portion of a steering mechanism for use in a modular catheter having the handle of either FIG. 4 or FIG. 5.

DETAILED DESCRIPTION OF EXEMPLARY EMBODIMENTS

Figure 3:
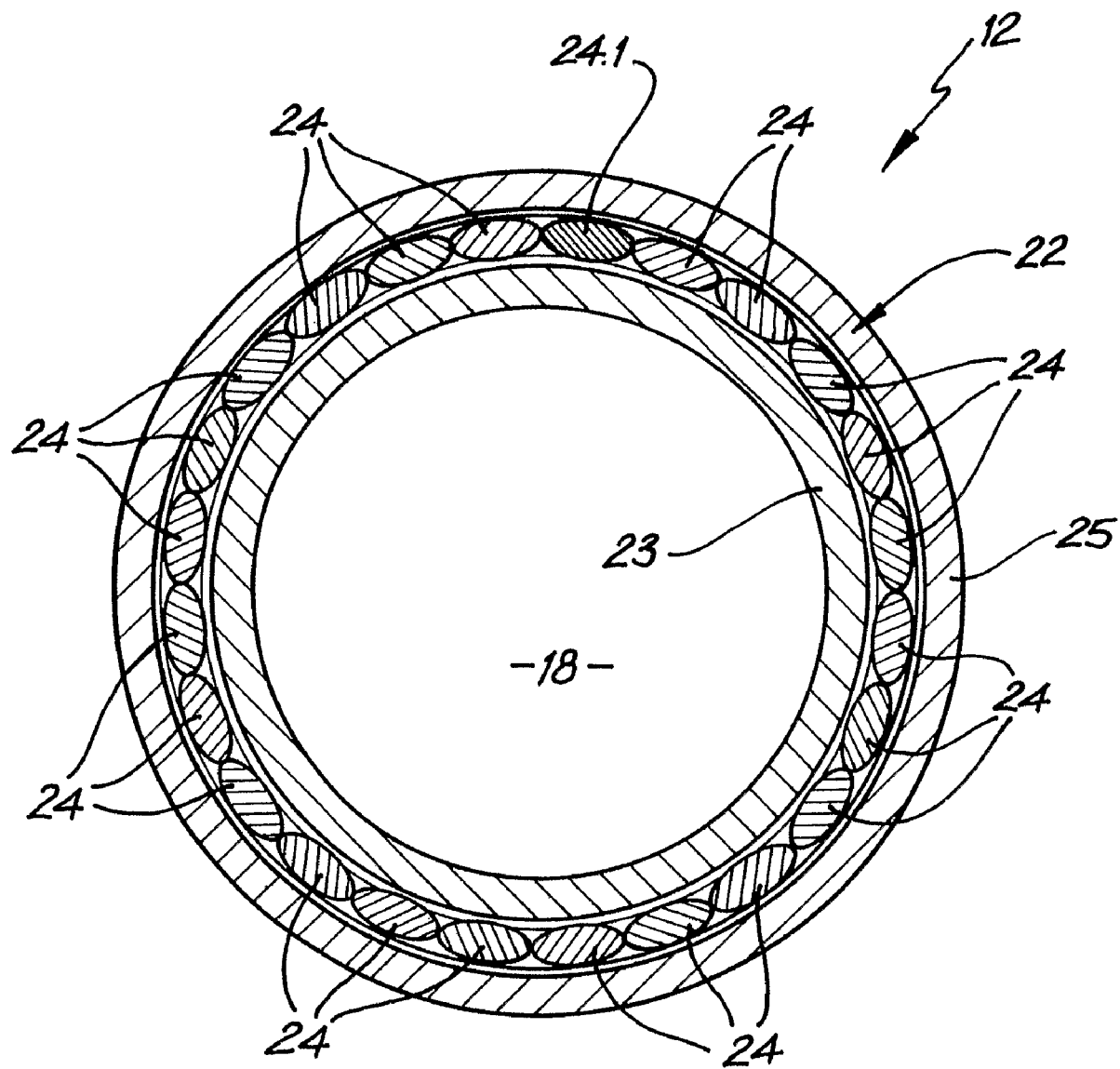
FIG. 3 shows, on an enlarged scale, a schematic, sectional end view of a tubular member of the modular catheter.

In FIGS. 1-3 of the drawings, reference numeral 10 generally designates a modular catheter, in accordance with an embodiment of the invention. The catheter 10 comprises an elongate tubular member 12 having a closed distal end or tip 14 and a proximal end 16. As shown more clearly in FIG. 2 of the drawings, the tubular member 12 defines a central lumen 18 extending from the proximal end 16 to the distal end 14 of the tubular member 12.

A plurality of electrodes 20 are arranged at, or proximate, the tip 14 of the tubular member 12.

As shown more clearly in FIG. 3 of the drawings, the tubular member 12 has a peripheral wall 22 in which conductors 24 are embedded. More particularly, the wall 22 comprises an inner tubular element 23, previously formed over a mandrel, about which the conductors 24 are helically wound. An outer layer 25 is cast over the conductors 24 to embed the conductors 24 and to form the wall 22 of the tubular member 12. Each electrode 20 has a conductor 24 associated with it. Additional conductors 24 may also be embedded in the wall 22 of the tubular member 12 to be used for temperature monitoring. For example, twenty-three conductors 24 may be provided for sensing purposes, i.e., connected to the electrodes 20, with one further conductor 24.1 being a Constantan thermocouple temperature-monitoring wire. Because the conductors 24 are arranged within the wall 22 of the tubular member 12, the lumen 18 is unimpeded by conductors 24 to the electrodes 20.

An electrical connector 26 is arranged at the proximal end 16 of the tubular member 12. The conductors 24 are connected to the electrical connector 26. The electrical connector 26 could be any suitable form of electrical connector such as, for example, an electrical plug-type arrangement, a slip-ring type arrangement, or the like. An example of an electrical connector 26 that can be used is a Redel plug-type connector available from Lemo Group Company of Ecublens, Switzerland. This type of connector has two mating connector bodies, one of which carries male connecting elements and the other of which carries female connecting elements.

The catheter 10 includes a shape-imparting or manipulating mechanism in the form of a steering mechanism 28. The steering mechanism 28 comprises a sheath 30, which is dimensioned to be a snug fit in the lumen 18 of the tubular member 12. In the embodiment shown in FIG. 2 of the drawings, the sheath 30 defines a secondary lumen 32 within which steering wires 34 are arranged. The steering wires 34 effect lateral displacement of the tip 14 of the tubular member 12 and control its radius of curvature to effect steering of the catheter 10 through veins of a patient's body and placement of the tip 14 of the tubular member 12 at the desired location in the patient's heart. Thus, a distal end 36 of the sheath 30 lies substantially in register with the tip 14 of the tubular member 12.

The connector bodies of the connector 26 are modified to allow the passage of the steering mechanism 28 through the bodies of the connector 26. Thus, each connector body has a bore formed through it, through which the steering mechanism 28 is able to pass. Each bore is optionally lined with a liner.

A coupling mechanism 38 is arranged at a proximal end of the steering mechanism 28. The coupling mechanism 38 couples the steering mechanism 28 releasably to a control device in the foam of a handle 40. More particularly, the coupling mechanism 38 couples the steering mechanism 28 to a control member in the form of a knurled thumb-wheel 42, or the like, of the handle 40 to effect lateral displacement of the distal tip 14 of the tubular member 12 via the steering mechanism 28, in use. In this regard, it is to be noted that the steering mechanism 28 is releasably connectable to the handle 40 independently of the tubular member 12.

The handle 40 of the catheter has a distal end 44 and a proximal end 46. The distal end 44 of the handle 40 has a complementary connector (not shown) for connecting to the electrical connector 26 of the tubular member 12. Similarly, the distal end 44 of the handle 40 has a complementary coupling member (also not shown) for coupling to the coupling mechanism 38 of the steering mechanism 28.

In addition, a connector is arranged at the proximal end 46 of the handle 40 for connection to a monitoring mechanism (not shown), as well as a source of ablation energy such as an RF source (also not shown), the monitoring mechanism and the leads for the RF energy together forming a patient cable. The connector at the proximal end preferably incorporates a slip ring arrangement or some similar form of rotation-permitting arrangement, to allow rotation of the handle 40 without rotating the patient cable. Instead of having the connector at the proximal end 46 of the handle 40, the patient cable could connect directly to the connector on the tubular member 12 rather than to the connector at the proximal end of the handle 46.

Referring to FIGS. 4-6 of the drawings, two further embodiments of the modular catheter 10 are described. With reference to FIGS. 1-3 of the drawings, like reference numerals refer to like parts unless otherwise specified.

In these embodiments of the catheter 10, the steering mechanism 28 is as described more fully in the applicant's U.S. Provisional Patent Application Ser. No. 60/599,720 entitled "A Steerable Catheter" filed on 5 Aug. 2004. The contents of U.S. Provisional Patent Application Ser. No. 60/599,720 are incorporated herein by reference.

In FIG. 4 of the drawings, a first embodiment of the handle 40 of the modular catheter 10 is shown. The handle 40 includes a cylindrical body 49 defining the distal end 44 and the proximal end 46. An actuator 50 is slidably arranged on the body 49 to be longitudinally displaceable along the body 49.

The body 49 defines a first receiving formation 52 in which a fastener (not shown), such as a grub screw, is receivable. Similarly, the actuator 50 defines an opening 54 through which a similar fastener (also not shown) is removably receivable.

As indicated above, the steering mechanism 28 is as described more fully in U.S. Provisional Patent Application Ser. No. 60/599,720. Thus, the steering mechanism 28 comprises an outer sheath 56 (FIG. 6) having a cutaway portion (not shown) at its distal end, as described in the referenced U.S. provisional patent application, to effect bending of the distal end. A steering wire 58 is received within the sheath 56.

A first securing formation 60 is carried on the sheath 56. The securing formation 60 defines a circumferentially arranged groove 62 in which the grub screw inserted through the opening 52 is received for securing the sheath to the body 49.

Similarly, a second securing formation 64, also defining a circumferentially arranged groove 66, is attached to the proximal end of the steering wire 58. The grub screw receivable through the opening 54 of the actuator 50 is received in the groove 66 for securing the proximal end of the wire 58 to the actuator 50. The opening 52 in the body 49 is arranged distally of the opening 54 in the actuator 50.

It will be noted that in this embodiment of the handle 40, the sheath 56 of the steering mechanism 28 is anchored to the body 49 and lateral displacement of the distal end of the steering mechanism 28 is achieved by displacement of the steering wire 58 relative to the sheath 56 by manipulating the actuator 50 in the direction of the arrows 68. Accordingly, when the actuator 50 is displaced relative to the body 49 in the direction of arrows 68, the steering wire 58 moves relative to the sheath 56 effecting lateral displacement of the distal end of the steering mechanism 28 and, in turn, the distal end of the tubular member 12.

A connector plug 70 is arranged at the distal end 44 of the body 49, which engages the connector 26 of the tubular member 12. A connector body 72 of the connector is received in the plug 70 for effecting electrical connection between the handle 40 and the mating connector body (not shown) of the connector 26 of the tubular member 12. As described above, a bore 74 is formed through the connector body 72 and the mating connector body of the connector 26 of the tubular member 12 through which the steering mechanism 28 passes.

Referring now to FIG. 5 of the drawings, yet a further embodiment of the handle 40 of the modular catheter 10 is shown. In this embodiment, the actuator 50 is arranged towards the distal end 44 of the handle 40 and the plug 70 is formed fast with the actuator 50 to be displaceable together with the actuator 50. The opening 52 of the body 49 is arranged proximally of the opening 54 of the actuator 50.

The actuator 50 is connected to the securing formation 60 of the sheath 56 of the steering mechanism 28 by inserting the grub screw through the opening 54 in the actuator 50. The cylindrical body 49 of the handle 40 is secured to the securing formation 64 of the steering wire 58 by inserting the grub screw through the opening 52 into the circumferential groove 66 of the formation 64.

With this arrangement, the steering wire 58 is anchored to the body 49 and does not move. Rather, lateral displacement of the distal end of the steering mechanism 28 is achieved by displacing the sheath 56 relative to the wire 58 as the actuator 50 is displaced in the direction of the arrows 68.

In use, the steering mechanism 28 is inserted into the lumen 18 of the tubular member 12 so that the distal end 36 of the steering mechanism 28 lies substantially in register with the tip 14 of the tubular member 12. The coupling mechanism 38 of the steering mechanism 28 is mechanically, but releasably, coupled to the handle 40 and its control member 42 or actuator 50, as the case may be. The connector 26 is electrically, but releasably, connected to the complementary connector at the distal end 44 of the handle 40. The catheter 10 so formed is then connected to the monitoring equipment and the source of ablation energy by connecting the patient cable to the connector at the proximal end 46 of the handle 40.

The clinician inserts the catheter into the patient's body and controls lateral displacement of the tip 14 of the tubular member 12 via the control member 42 or actuator 50. Once positioned, the catheter 10 is used for monitoring and/or ablative purposes.

After use, once the catheter 10 has been removed from the patient's body, the catheter 10 is disassembled by disconnecting the connector 26 from the handle 40 and, similarly, decoupling the coupling member 38 from the handle 40. The tubular member 12, having been in contact with bodily fluids of the patient, is disposed of. The handle 40 and the steering mechanism 28, not having been in contact with any bodily fluids of the patient, is re-usable after sterilization, if necessary.

Further to inhibit the likelihood of contamination of the catheter 10 by a patient's bodily fluids, the catheter 10 optionally includes a cover member in the form of a plastics or elastomeric cover 48, which is a snug fit over the handle 40 to inhibit the access of bodily fluids into the switch gear of the handle 40. Similarly, for the embodiments of FIGS. 4 and 5 of the drawings, plugs (not shown) are provided for plugging the openings 52 and 54 after insertion of the grub screws to inhibit the ingress of bodily fluids into the interior of the handle 40.

It is also to be noted that, in another embodiment of the invention, at least the steering mechanism 28 and, optionally, the handle 40 can be replaced by a stylet (not shown), which may also be disposable, which is received in the lumen 18 of the tubular member 12. The stylet may have a predetermined curvature imparted thereto. This curvature may, in turn, be imparted to the tubular member 12 to form a fixed curve catheter.

It is a particular advantage of the invention that a modular catheter 10 is provided. Because only the tubular member 12 is disposable, the cost of such a catheter 10 is significantly lowered as the whole catheter, including its handle and steering mechanism, need not be disposed of after a single use. In fact, the handle 40 and the steering mechanism 20 can be re-used an indefinite number of times and the only part that requires replacement for each use is the tubular member 12.

In addition, the versatility of the system is substantially increased as the clinician can make use of tubular members 12 having different electrode configurations for different applications. Thus, the modular catheter 10 could include a range of tubular members 12, each having different configurations of electrodes 20 for different applications. It will be appreciated that, with this arrangement, the connector 26 with the associated connector 44 of the handle 40 would be a universal-type connector 26 to cater for the different ranges of electrode configurations. For a catheter 10 with a small number of electrodes 20, this would mean some of the pins in the proximal connector would not be used.

In addition, different steering mechanisms 28 can also be used by replacing one steering mechanism 28 with a steering mechanism 28 having a different characteristic. This, further improves the versatility of the modular catheter 10 of the present invention. For example, a steering mechanism 28 having a distal end 36 that can bend to a first predetermined radius of curvature may be replaced by a second steering mechanism 28, which has a distal end 36 that can be bent to a second, larger or smaller, radius of curvature and/or a different shape of curve than that of the first steering mechanism 28.

Still further, the modular catheter 10 of the present invention could include handles 40 having different types of controls, each type of handle 40 being a re-usable handle.

It is to be emphasized that, because the tubular member 12 is the only part of the catheter 10 that is used only once, the cost of the modular catheter 10 is significantly reduced over the long term as the handle 40 and the steering mechanism 28 are re-useable.

Yet a further major advantage of the invention is that, because the lumen of the tubular member 12 is unimpeded by conductors, the steering mechanism 28 is a tight or snug fit in the lumen of the tubular member 12. As a result, very accurate and fine control of the distal end of the tubular member 12 can be achieved as there is very little, if any, lost lateral motion of the steering mechanism 28 relative to the tubular member 12.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A modular catheter, which includes:
   an elongate tubular member having a proximal end and a closed, distal end with a lumen extending from the proximal end to the distal end and a plurality of electrodes arranged at, or adjacent, the distal end, conductors for the electrodes being contained within a wall of the tubular member;
   an elongate steering mechanism removably received within the lumen of the tubular member such that a distal end of the steering mechanism is substantially in register with the distal end of the tubular member, wherein the steering mechanism is configured for controlling lateral displacement of the distal end of the tubular member; and
   a control device having a proximal end and a distal end, the proximal end of the tubular member and a proximal end of the steering mechanism being releasably connectable to the distal end of the control device.

2. The modular catheter of claim 1, in which the steering mechanism and the tubular member are releasably connectable to the control device independently of each other.

3. The modular catheter of claim 1, in which the steering mechanism has an outer diameter approximating that of a diameter of the lumen of the tubular member to be a snug fit within the lumen of the tubular member.

4. The modular catheter of claim 1, in which the proximal end of the tubular member carries a connector thereon for connection to a corresponding connector of the control device.

5. The modular catheter of claim 1, in which a proximal end of the steering mechanism carries a coupling mechanism for effecting releasable mechanical coupling to the control device and to a manipulating element of the control device.

6. The modular catheter of claim 5, in which the manipulating element is an actuator, which is linearly displaceable relative to a body of the control device.

7. The modular catheter of claim 6, in which the coupling mechanism has a first securing formation releasably connectable to the body of the control device and a second securing formation releasably connectable to the actuator so that displacement of the securing formations relative to each other causes lateral displacement of the distal end of the steering mechanism and, hence, the distal end of the tubular member.

8. The modular catheter of claim 1, which includes a disposable covering member for the control device.

9. The modular catheter of claim 1, in which the steering mechanism is a stylet, which is received in the lumen of the tubular member.

10. A modular catheter, which includes:
    an elongate tubular member having a proximal end and a closed, distal end with a lumen extending from the proximal end to the distal end and a plurality of electrodes arranged at, or adjacent, the distal end, conductors for the electrodes being contained within a wall of the tubular member;
    an elongate steering mechanism removably received within the lumen of the tubular member such that a distal end of the steering mechanism is substantially in register with the distal end of the tubular member, wherein the steering mechanism is configured for controlling lateral displacement of the distal end of the tubular member; and
    an elongate control device having a proximal end and a distal end, the proximal end of the tubular member and a proximal end of the steering mechanism being releasably connectable to the distal end of the control device, the control device carrying an actuator thereon, which is displaceable along a longitudinal axis of the control device for controlling displacement of the distal end of the steering mechanism to effect displacement of the distal end of the tubular member.

11. A modular catheter, which includes:
    an elongate tubular member having a proximal end and a closed, distal end with a lumen extending from the proximal end to the distal end and a plurality of electrodes arranged at, or adjacent, the distal end, conductors for the electrodes being contained within a wall of the tubular member;

an elongate steering mechanism removably received within the lumen of the tubular member such that a distal end of the steering mechanism is substantially in register with the distal end of the tubular member, wherein the steering mechanism is configured for controlling lateral displacement of the distal end of the tubular member; and a control device having a proximal end and a distal end, the proximal end of the tubular member and a proximal end of the steering mechanism being releasably connectable to the distal end of the control device, the control device including a body and an actuator displaceably arranged on the body, a proximal end of the steering mechanism carrying a first securing formation releasably connectable to the actuator and a second securing formation releasably connectable to the body.

* * * * *

UNITED STATES PATENT AND TRADEMARK OFFICE
CERTIFICATE OF CORRECTION

| | | |
|---|---|---|
| PATENT NO. | : 8,064,978 B2 | |
| APPLICATION NO. | : 10/580636 | |
| DATED | : November 22, 2011 | |
| INVENTOR(S) | : Neil L. Anderson et al. | |

It is certified that error appears in the above-identified patent and that said Letters Patent is hereby corrected as shown below:

In the specification:

| | | |
|---|---|---|
| COLUMN 3, | LINE 61, | change "handle" to --control device-- |
| COLUMN 4, | LINE 60, | change "foam" to --form-- |
| COLUMN 5, | LINE 1, | change "catheter has" to --catheter 10 has-- |
| COLUMN 5, | LINE 8, | change "connector" to --connector (not shown)-- |
| COLUMN 5, | LINE 12, | change "RF energy" to --RF source-- |
| COLUMN 5, | LINE 13, | change "proximal end" to --proximal end 46-- |
| COLUMN 5, | LINE 18, | change "connector" to --connector 26-- |
| COLUMN 5, | LINE 19, | change "proximal end" to --proximal end 46-- |
| COLUMN 5, | LINE 20, | change "handle 46." to --handle 40.-- |
| COLUMN 5, | LINE 52, | change "the sheath" to --the sheath 56-- |
| COLUMN 5, | LINE 58, | change "of the wire" to --of the steering wire-- |
| COLUMN 5, | LINE 63, | change "distal end" to --distal end 36-- |
| COLUMN 6, | LINE 2, | change "distal end" to --distal end 36-- |
| COLUMN 6, | LINE 3, | change "distal end" to --distal end 14-- |
| COLUMN 6, | LINE 27, | change "formation" to --securing formation-- |
| COLUMN 6, | LINE 30, | change "distal end" to --distal end 36-- |
| COLUMN 6, | LINE 31, | change "to the wire" to --to the steering wire-- |
| COLUMN 6, | LINE 40, | change "connector at the" to --connector plug 70 at the-- |
| COLUMN 6, | LINE 45, | change "catheter" to --catheter 10-- |
| COLUMN 6, | LINE 53, | change "member 38 from" to --mechanism 38 from-- |
| COLUMN 6, | LINE 57, | change "is re-usable after" to --are re-usable after-- |
| COLUMN 6, | LINE 58, | change "Further to inhibit" to --To further inhibit-- |
| COLUMN 6, | LINE 60, | change "plastics" to --plastic-- |
| COLUMN 7, | LINE 12, | change "lowered as the whole catheter, including its handle" to --lowered as the whole catheter 10, including its handle 40-- |
| COLUMN 7, | LINE 13, | change "mechanism," to --mechanism 28,-- |
| COLUMN 7, | LINE 14, | change "mechanism 20" to --mechanism 28-- |

Signed and Sealed this
Third Day of June, 2014

Michelle K. Lee
*Deputy Director of the United States Patent and Trademark Office*

CERTIFICATE OF CORRECTION (continued)
U.S. Pat. No. 8,064,978 B2

In the specification (continued):

| | | |
|---|---|---|
| COLUMN 7, | LINE 24, | change "connector 44" to --connector plug 70-- |
| COLUMN 7, | LINE 48, | change "lumen" to --lumen 18-- |
| COLUMN 7, | LINE 50, | change "lumen" to --lumen 18-- |
| COLUMN 7, | LINE 51, | change "distal end" to --distal end 14-- |

In the claims:

| | | |
|---|---|---|
| CLAIM 5, | COLUMN 8, LINE 23, | change "a proximal end" to --the proximal end-- |
| CLAIM 11, | COLUMN 10, LINE 6, | change "a proximal end" to --the proximal end-- |